(12) United States Patent
Amdursky et al.

(10) Patent No.: US 12,217,884 B2
(45) Date of Patent: Feb. 4, 2025

(54) PROTEIN-BASED FILMS

(71) Applicant: TECHNION RESEARCH & DEVELOPMENT FOUNDATION LIMITED, Haifa (IL)

(72) Inventors: Nadav Amdursky, Haifa (IL); Ramesh Nandi, Haifa (IL)

(73) Assignee: TECHNION RESEARCH & DEVELOPMENT FOUNDATION LIMITED, Haifa (IL)

(*) Notice: Subject to any disclaimer, the term of this patent is extended or adjusted under 35 U.S.C. 154(b) by 265 days.

(21) Appl. No.: 17/772,812

(22) PCT Filed: Oct. 29, 2020

(86) PCT No.: PCT/IL2020/051128
§ 371 (c)(1),
(2) Date: Apr. 28, 2022

(87) PCT Pub. No.: WO2021/084538
PCT Pub. Date: May 6, 2021

(65) Prior Publication Data
US 2023/0005640 A1 Jan. 5, 2023

Related U.S. Application Data

(60) Provisional application No. 62/927,152, filed on Oct. 29, 2019.

(51) Int. Cl.
*C07K 14/76* (2006.01)
*H01B 1/12* (2006.01)

(52) U.S. Cl.
CPC ............ *H01B 1/122* (2013.01); *C07K 14/76* (2013.01)

(58) Field of Classification Search
CPC . H04L 12/281; H04L 12/2816; H04L 41/082; H04L 41/0893; H04L 61/5069; H04L 67/12; C07K 14/76; C07K 14/765; H01B 1/122; Y02E 10/549; H10K 85/761
See application file for complete search history.

(56) References Cited

U.S. PATENT DOCUMENTS 9,950,093 B2 * 4/2018 Zussman ................ A61L 27/26

OTHER PUBLICATIONS

Amdursky, N., Marchak, D., Sepunaru, L., Pecht, I., Sheves, M. and Cahen, D. (2014), Electronic Transport via Proteins. Adv. Mater., 26: 7142-7161. https://doi.org/10.1002/adma.201402304.
Amdursky, N., Wang, X., Meredith, P., Bradley, D.D.C. and Stevens, M.M. (2016), Long-Range Proton Conduction across Free-Standing Serum Albumin Mats. Adv. Mater., 28: 2692-2698. https://doi.org/10.1002/adma.201505337.
Amdursky, N., Wang, X., Meredith, P., Riley, D. J., Payne, D. J., Bradley, D. D. C., Stevens, M. M., Electron Hopping Across Hemin-Doped Serum Albumin Mats on Centimeter-Length Scales. Adv. Mater. 2017, 29, 1700810. https://doi.org/10.1002/adma.201700810.

(Continued)

*Primary Examiner* — Lawrence D Ferguson
(74) *Attorney, Agent, or Firm* — The Roy Gross Law Firm, LLC; Roy Gross

(57) ABSTRACT

Protein based highly stretchable compositions with ionic conductivity are disclosed herein. Methods for preparing such compositions are also disclosed.

13 Claims, 11 Drawing Sheets

(56) References Cited

OTHER PUBLICATIONS

Nandi, R., Agam, Y., Amdursky, N., A Protein-Based Free-Standing Proton-Conducting Transparent Elastomer for Large-Scale Sensing Applications. Adv. Mater. 2021, 33, 2101208. https://doi.org/10.1002/adma.202101208.
PCT International Search Report for International Application No. PCT/IL2020/051128, mailed Feb. 11, 2021, 2pp.
PCT Written Opinion for International Application No. PCT/IL2020/051128, mailed Feb. 11, 2021, 5pp.
PCT International Preliminary Report on Patentability for International Application No. PCT/IL2020/051128, issued May 3, 2022, 6pp.

* cited by examiner

PROTEIN-BASED FILMS

CROSS REFERENCE TO RELATED APPLICATIONS

This application is a National Phase of PCT Patent Application No. PCT/IL2020/051128 having International filing date of Oct. 29, 2020, which claims the benefit of priority under 35 U.S.C. § 119 (e) of U.S. Provisional Patent Application No. 62/927,152, filed on Oct. 29, 2019. The contents of the above applications are all incorporated by reference as if fully set forth herein in their entirety.

FIELD OF THE INVENTION

The present invention is in the field of protein-based polymer films and semiconductors.

BACKGROUND OF THE INVENTION

In recent years there is extensive use of electronic materials and devices. One of the main problems when dealing with existing electronics is the fact that they are made out of Si-based semiconductor and metallic electrode, which are not flexible, expensive and most of all not bio-degradable.

To deal with millions of tons of e-waste there is an increasing need for biodegradable materials to replace conventional electronics materials. Further, cellular interfacing of electronics for bionics application require biocompatible material, which can efficiently transfer signal to the electrodes.

SUMMARY OF THE INVENTION

The present invention, in some embodiments thereof, relates to protein based highly stretchable compositions with ionic conductivity.

According to an aspect of the present invention, there is provided a composition comprising an at least partially denatured protein and one or more crosslinkers, wherein the composition is characterized by a conductivity in the range of 0.1 mS cm$^{-1}$ to 1.5 mS cm$^{-1}$.

In some embodiments, the composition is characterized by a transparency in the range of 95% to 100%.

In some embodiments, the composition is characterized by a Young's Modulus in the range of 1 MPa to 50 MPa.

In some embodiments, the composition is characterized by an elastic limit in the range of 100% to 600%.

In some embodiments, the crosslinker comprises an amine, diamine or dithiol.

In some embodiments, the at least partially denatured protein is crosslinked via amine bonds or disulfide bonds.

In some embodiments, the partially denatured protein is characterized by a conductance threshold of at least 0.1 mS cm$^{-1}$.

In some embodiments, the partially denatured protein comprises albumin.

In some embodiments, the partially denatured protein and the crosslinker are in a weight per weight (w/w) ratio of 100:0.01 to 100:1.

In some embodiments, the composition further comprises one or more denaturing agents.

In some embodiments, the denaturing agents are selected from the group consisting of a disulfide bond reducing agent, a chaotropic agent, or a combination thereof.

In some embodiments, the composition comprises 0.01% to 25% (w/w) of the disulfide bond reducing agent.

In some embodiments, the disulfide bond reducing agent comprises one or more thiol containing reducing agent, including but not limited to 2-mercaptoethanol, dithiothreitol (DTT), (tris(2-carboxyethyl)phosphine) (TCEP), cysteine, glutathione, a phosphine-containing agent or a combination thereof.

In some embodiments, the composition is in the form of a film, a fiber, or a bioink.

In some embodiments, the composition is characterized by a fluorescence emission in the range of 350 nm to 750 nm.

In some embodiments, the composition further comprises a dopant.

In some embodiments, the dopant is selected from a polymer, an organic molecule, an inorganic molecule, an inorganic nanocrystal, a nanowire, and any combination thereof.

In some embodiments, the composition further comprises a chemical modification.

In some embodiments, the chemical modification is selected from fluorination, sulfonation, phosphorylation, carboxylation, amide bond formation, glycosylation, or any combination thereof.

In some embodiments, the composition further comprises a light activated molecule.

In some embodiments, the light activated molecule is selected from a photobase generator or a photoacid generator.

In some embodiments, the composition is characterized by a conductivity in the range of 1.5 mS cm$^{-1}$ to 100 mS cm$^{-1}$.

In some embodiments, the composition is for use in fuel cell configuration, optogenetics, tissue engineering, organic field effect transistors (OFET), organic light emitting diodes (OLED), organic photovoltaic cells (OPV), flexible electronics, electrodes, implantable electronic devices (CIEDs), or electrodes for human machine interfaces (HMI).

According to an aspect of the present invention, there is provided an article comprising a composition according to the present invention.

In some embodiments, the composition has a thickness in the range of 1 μm to 1000 μm.

In some embodiments, the article is selected from the group consisting of: an electronic device, an optical device, a medical device and a mechanical device.

According to an aspect of the present invention, there is provided a method for preparing a composition according to the present invention, comprising: a. contacting a protein in a solvent, thereby obtaining a solution; b. contacting the solution with one or more denaturing agents and a crosslinker; and c. allowing the solvent to evaporate, thereby forming the composition according to the present invention.

In some embodiments, the solvent comprises 2,2,2-Trifluoroethanol (TFE), water or a combination thereof.

In some embodiments, the TFE and water are used in a ratio of 100% TFE to 1:1 (TFE:water).

In some embodiments, the protein and the crosslinker are used in a ratio of 100:0.01 to 100:1.

In some embodiments, the method comprises the step of d. contacting the composition with a dopant, a chemical modification, a light activated molecule or any combination thereof.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

Further embodiments and the full scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
FIG. 1 presents a picture of a free standing transparent bovine serum albumin (BSA) film.

According to some embodiments, the present invention is directed to compositions comprising natural proteins as electron and ionic conductors.

According to an aspect of some embodiments of the present invention there is provided a composition comprising an at least partially denatured protein and one or more crosslinkers. In some embodiments, the composition is in the form of a transparent, stretchable, conductive and biocompatible film.

In some embodiments, the present invention is directed to methods of preparing a composition of the present invention. In some embodiments, the method is a single pot method. In some embodiments, the preparation method is devoid of complex equipment, such as electrospinning equipment, printer, or synthesis-related equipment.

Compositions

According to an aspect of some embodiments of the present invention there is provided a composition comprising an at least partially denatured protein and one or more crosslinkers, wherein the composition is characterized by a conductivity in the range of 0.1 mS cm$^{-1}$ to 1.5 mS cm$^{-1}$. In some embodiments, a composition according to the present invention is characterized by a conductivity in the range of 0.1 mS cm$^{-1}$ to 1.4 mS cm$^{-1}$, 0.1 mS cm$^{-1}$ to 1.3 mS cm$^{-1}$, 0.1 mS cm$^{-1}$ to 1.2 mS cm$^{-1}$, 0.1 mS cm$^{-1}$ to 1.1 mS cm$^{-1}$, 0.1 mS cm$^{-1}$ to 1.0 mS cm$^{-1}$, 0.2 mS cm$^{-1}$ to 1.5 mS cm$^{-1}$, 0.3 mS cm$^{-1}$ to 1.5 mS cm$^{-1}$, or 0.5 mS cm$^{-1}$ to 1.5 mS cm$^{-1}$, including any range therebetween. In some embodiments, conductivity is ionic conductivity. In some embodiments, the conductivity is protonic conductivity. In some embodiments, conductivity is electrical conductivity.

The term "conductivity" as used herein, refers to the ability of a material to conduct electricity, heat, fluid or sound. In some embodiments, conductivity refers to the ability of a material to conduct electric current.

The term "conductance" as used herein, refers to a measurement of how easily a current can flow through a component. It must be noted that conductance is a property of the component itself. The conductance is defined as the inverse of resistance.

According to an aspect of some embodiments of the present invention there is provided a composition comprising an at least partially denatured protein and one or more crosslinkers, wherein the composition is characterized by a transparency in the range of 95% to 100%. In some embodiments, a composition according to the present invention is characterized by a transparency in the range of 96% to 100%, 97% to 100%, 98% to 100%, 99% to 100%, 99.5% to 100%, or 99.9% to 100%, including any range therebetween. In some embodiments, a composition according to the present invention is characterized by a transparency of 99%. %. In some embodiments, a composition according to the present invention is characterized by a transparency of 100%.

In some embodiments, a composition according to the present invention is characterized by a light transmission of more than 85%, more than 90% more than 95%, or more than 98%. In some embodiments, a composition according to the present invention is characterized by a light transmission in the range of 85% to 100%, 90% to 100%, 95% to 100%, or 99% to 100%, including any range therebetween.

In some embodiments, a composition according to the present invention is characterized by a light transmission of 98%. In some embodiments, a composition according to the present invention is characterized by a light transmission of 99%. In some embodiments, a composition according to the present invention is characterized by a light transmission of 100%.

In some embodiments, the optical transparence and clarity of the composition can be quantitatively defined by parameters including light transmission.

As used herein, "transparency" (or transmission of visible light) is characterized by light transmittance, i.e. the measured percentage of incident light transmitted through a composition or material.

As used herein, "light transmission" refers to the percentage of an incident light transmitted through a medium. In some embodiments, the incident light comprises visible light having a wavelength between 400 nm to 700 nm including any value therebetween. In some embodiments, the light transmission of the composition is at least 50%, at least 60%, at least 70%, at least 80%, or at least 85%, at least 90%, at least 95%, at least 98%, or at least 99%, including any value therebetween.

According to an aspect of some embodiments of the present invention there is provided a composition comprising an at least partially denatured protein and one or more crosslinkers, wherein the composition is characterized by a Young's Modulus in the range of 1 MPa to 50 MPa. In some embodiments, there is provided a composition comprising a crosslinked partially denatured protein, wherein the composition is characterized by a Young's Modulus in the range of 1 MPa to 50 MPa. In some embodiments, a composition according to the present invention is characterized a Young's Modulus in the range of 1 MPa to 45 MPa, 1 MPa to 43 MPa, 1 MPa to 40 MPa, 1 MPa to 35 MPa, 1 MPa to 33 MPa, 1 MPa to 30 MPa, 1 MPa to 25 MPa, 1 MPa to 23 MPa, 1 MPa to 20 MPa, 1 MPa to 15 MPa, 1 MPa to 13 MPa, 1 MPa to 10 MPa, 2 MPa to 20 MPa, 5 MPa to 20 MPa, 5 MPa to 50 MPa, or 2 MPa to 15 MPa, including any range therebetween.

As used herein, the term "Young's Modulus" refers to a quantification of the stiffness of a given material. Young's modulus, E, can be calculated by dividing the tensile stress by the tensile strain.

According to some embodiments of the present invention, there is provided a composition comprising an at least partially denatured protein and one or more crosslinkers, wherein the composition is characterized by an elastic limit in the range of 100% to 600%. In some embodiments, a composition according to the present invention is characterized by an elastic limit in the range of 100% to 550%, 100% to 540%, 100% to 500%, 100% to 480%, 100% to 450%, 100% to 430%, 150% to 500%, or 200% to 500%, including any range therebetween.

As used herein, the term "elastic" refers to any material which can be stretched or deformed and return to its original shape without substantial permanent deformation. In some embodiments, "elastic" refers to any material which, upon application of a biasing force, is stretchable, that is, elongatable, to a stretched, biased length which is at least about 60 percent (i.e., to a stretched, biased length, which is at least about 160 percent of its relaxed unbiased length), and which, will recover at least 30 percent of its elongation upon release of the stretching, elongating force.

As used herein, the term "elastic limit" refers to the maximum stress or force per unit area within a material that can arise before failure.

The term "crosslinked", as used herein, refers to the formation of a chemical bond between two molecules. In some embodiments, crosslinked is inter crosslinked (e.g. via a chemical bond formed between a plurality of side chains within the same protein molecule). In some embodiments, crosslinked is intra crosslinked (e.g. via a chemical bond formed between a plurality of side chains of different protein molecules). In some embodiments, crosslinked comprises intra cross-linking and inter cross-linking.

The term "crosslinker", as used herein, refers to the element, group, or compound that effects cross-linking between two molecules (e.g. side chains within the same or different protein molecules).

In some embodiments, a protein comprises albumin. In some embodiments, a protein comprises bovine serum albumin. In some embodiments, a protein comprises human derived serum albumin. In some embodiments, a protein is a partially denatured protein. In some embodiments, a partially denatured protein comprises albumin. In some embodiments, a partially denatured protein comprises bovine serum albumin. In some embodiments, a partially denatured protein comprises human derived serum albumin.

In some embodiments, the partially denatured protein is a fragment of human derived serum albumin. In some embodiments, the partially denatured protein is a fragment of 20 amino acids, 30 amino acids, 40 amino acids, 50 amino acids, 60 amino acids, 70 amino acids, 80 amino acids, 90 amino acids, 100 amino acids, 120 amino acids, 140 amino acids, 160 amino acids, 180 amino acids, 200 amino acids, 240 amino acids, 280 amino acids, 320 amino acids, 350 amino acids, 400 amino acids, 450 amino acids, 500 amino acids, 550 amino acids, 600 amino acids, including any value therebetween. In some embodiments, the partially denatured protein is a fragment of 100-200 amino acids, 240-600 amino acids, including any range therebetween. In some embodiments, the partially denatured protein comprises at least 50% sequence identity to all or a portion of human serum albumin. In some embodiments, the partially denatured protein comprises at least 60%, at least 70%, at least 75%, at least 80%, at least 85%, at least 90%, at least 95%, at least 99% sequence identity to all or a portion of human serum albumin, including any value therebetween.

In some embodiments, the partially denatured protein is a fragment of bovine serum albumin. In some embodiments, the partially denatured protein is a fragment of 20 amino acids, 30 amino acids, 40 amino acids, 50 amino acids, 60 amino acids, 70 amino acids, 80 amino acids, 90 amino acids, 100 amino acids, 120 amino acids, 140 amino acids, 160 amino acids, 180 amino acids, 200 amino acids, 240 amino acids, 280 amino acids, 320 amino acids, 350 amino acids, 400 amino acids, 450 amino acids, 500 amino acids, 550 amino acids, 600 amino acids, of bovine serum albumin, including any value therebetween. In some embodiments, the partially denatured protein is a fragment of 100-200 amino acids, 240-600 amino acids, of bovine serum albumin, including any range therebetween. In some embodiments, the partially denatured protein comprises at least 50% sequence identity to all or a portion of bovine serum albumin. In some embodiments, the partially denatured protein comprises at least 60%, at least 70%, at least 75%, at least 80%, at least 85%, at least 90%, at least 95%, at least 99% sequence identity to all or a portion of bovine serum albumin, including any value therebetween. The present invention is not limited to these variants of albumin, and other albumins (e.g., other serum albumins, storage protein ovalbumin, etc.).

In some embodiments, a composition according to the present invention comprises two or more types of albumin or variations (e.g., fragments) of a single albumin (e.g., human serum albumin).

As used herein, the terms "peptide", "polypeptide" and "protein" are used interchangeably to refer to a polymer of amino acid residues. The terms "peptide", "polypeptide" and "protein" as used herein encompass native peptides, peptidomimetics (typically including non-peptide bonds or other synthetic modifications) and the peptide analogs peptoids and semi-peptoids or any combination thereof. In another embodiment, the terms "peptide", "polypeptide" and "protein" apply to amino acid polymers in which at least one amino acid residue is an artificial chemical analog of a corresponding naturally occurring amino acid. Functional fragments of a polypeptide or protein refers to all fragments of a polypeptide or protein that retain an activity, or a measurable portion of an activity, of the polypeptide or protein from which the fragment is derived. Fragments, for example, can vary in size from a polypeptide fragment as small as an epitope capable of binding an antibody molecule to a large polypeptide capable of participating in the characteristic induction or programming of phenotypic changes within a cell.

As used herein, the term "denatured" refers to a protein that has a loss of structural order of at least some of the protein's secondary, tertiary or quaternary structure. This may include the breaking of cross-linking or interactions, such as disulfide bonds, electrostatic forces, hydrogen bonding and other protein interactions such as Van Der Waal forces, or any other protein-protein interactions between different portions of a protein structure or adjacent proteins.

In some embodiments, an at least partially denatured protein is characterized by a conductance threshold of at least 0.1 mS cm$^{-1}$. In some embodiments, an at least partially denatured protein has a conductance threshold of at least 0.12 mS cm$^{-1}$, 0.15 mS cm$^{-1}$, 0.17 mS cm$^{-1}$, 0.19 mS cm$^{-1}$, 0.2 mS cm$^{-1}$, 0.25 mS cm$^{-1}$, 0.3 mS cm$^{-1}$, 0.35 mS cm$^{-1}$, 0.4 mS cm$^{-1}$, 0.45 mS cm$^{-1}$, or 0.5 mS cm$^{-1}$, including any value therebetween.

In some embodiments, a crosslinker comprises an amine, diamine or a dithiol. In some embodiments, the crosslinker comprises a reactive group capable of forming a covalent bond with a side chain of the protein. In some embodiments, the crosslinker comprises a plurality of reactive groups. In some embodiments, the crosslinker comprises a plurality of reactive groups wherein the reactive group are the same or different.

In some embodiments, the crosslinker comprises the reactive group selected from an amine, a sulfide, an ester (e.g. an active ester such as N-hydroxy succinimide ester), a succinimide, a maleimide, a Michael acceptor (e.g. 1,4 unsaturated carbonyl), a halo group, an aldehyde, an acyl halide, a hydroxy group or any combination thereof.

In some embodiments, the crosslinker comprises an alkyl bound to at least one reactive group, wherein the reactive group is as described herein. In some embodiments, the alkyl is optionally substituted. In some embodiments, the crosslinker comprises an alkyl bound to a plurality of reactive groups.

In some embodiments, the alkyl comprises between 1 and 20, between 1 and 3, between 3 and 5, between 5 and 7, between 7 and 10, between 10 and 15, between 15 and 20 methylene units, including any range or value therebetween.

In some embodiments, a crosslinker comprises 1,2-ethanedithiol. In some embodiments, a crosslinker comprises ethylenediamine. In some embodiments, a crosslinker comprises methyl amine, di-methyl amine, tri-methyl amine, or any combination thereof.

In some embodiments, an at least partially denatured protein is crosslinked via a bond selected form an amine bond a disulfide bond, an amide bond, or any combination thereof.

In some embodiments, a composition according to the present invention comprises a partially denatured protein and a crosslinker are in a ratio of 100:0.01 to 100:1. In some embodiments, a composition according to the present invention comprises a partially denatured protein and a crosslinker are in a ratio of 100:0.05 to 100:1, 100:0.1 to 100:1, 100:0.15 to 100:1, 100:0.2 to 100:1, 100:0.1 to 100:0.5, 100:0.1 to 100:0.15, 100:0.1 to 100:0.2, or 100:0.1 to 100:0.9, including any range therebetween.

In some embodiments, a composition according to the present invention, further comprising one or more denaturing agents.

As used herein, the term "denaturing agents" refers to substances that affect the structure of proteins. In some embodiments, the denaturing agent may be any agent which results in the denaturation of proteins into a lower structured or folded protein than the original protein. This group includes but is not limited to reducing agents, which disrupt the disulfide bonds in proteins, and chaotropic agents, which disrupt the hydrogen bonds in proteins.

In some embodiments, the denaturing agent may be a combination of two or more denaturing agents. In some embodiments, the denaturing agents are present in an amount sufficient to at least disrupt tertiary structure of the protein. In some embodiments, the denaturing agents are present in an amount sufficient to disrupt tertiary and quaternary structures of the protein.

In some embodiments, the denaturing agent may act to disrupt or break all protein-protein interactions such that the protein is in a fully unfolded, or secondary structure configuration.

In some embodiments, the protein may retain some of its secondary, tertiary, or quaternary structure.

In some embodiments, denaturing agents are selected from the group consisting of a disulfide bond reducing agent, a chaotropic agent, or a combination thereof.

In some embodiments, the composition comprises 0.01% to 25% (w/w), 0.09% to 25% (w/w), 0.1% to 25% (w/w), 0.5% to 25% (w/w), 1% to 25% (w/w), 5% to 25% (w/w), 10% to 25% (w/w), or 15% to 25% (w/w), of the disulfide bond reducing agent, including any range therebetween.

In some embodiments, denaturing agent is a disulfide bond reducing agent. In some embodiments, a disulfide bond reducing agent comprises one or more thiol containing reducing agent, including but not limited to 2-mercaptoethanol, dithiothreitol (DTT), tris(2-carboxyethyl)phosphine) (TCEP), cysteine, glutathione, a phosphine-containing agent or a combination thereof.

In some embodiments, a composition according to the present invention is in the form of a film, a fiber, or a bioink. In some embodiments, the composition is in the form of a film. The term "film" as used herein refers to a continuous, homogenous, dimensionally stable material having a small thickness in relation to area.

In some embodiments, a composition according to the present invention has a fluorescence emission in the range of 350 nm to 750 nm. In some embodiments, a composition according to the present invention has a fluorescence emission in the range of 350 nm to 700 nm, 350 nm to 690 nm, 350 nm to 680 nm, 350 nm to 670 nm, 350 nm to 660 nm, 350 nm to 650 nm, or 370 nm to 630 nm, including any range therebetween.

In some embodiments, a composition according to the present invention, further comprises a dopant. In some embodiments, a dopant is selected from a polymer, an organic molecule, an inorganic molecule, an inorganic nanocrystal, a nanowire, and any combination thereof.

In some embodiments, the dopant is an inorganic molecule selected from the group consisting of: a metal chalcogenide, a small metal cluster, a light-emitting molecule, and any combination thereof. In some embodiments, the dopant is an inorganic molecule (i.e. an inorganic dopant), wherein a concentration of the inorganic dopant within the composition is between $10^{-3}$ and $10^{-6}$ M. Various inorganic dopants are well-known in the art. In some embodiments, the dopant is selected from grapheme, carbon nanotubes (CNTs), fullerene (C60) and their derivatives.

In some embodiments, the dopant is an organic molecule selected from the group consisting of: an organic dye (e.g. a cyanine dye, such as Cy-5, Cy-7, and Cy-3 etc.; rhodamine, FITC, or any other dye well-known in the art), a porphyrin-based molecule (e.g. hemin, platinum-octaethylporphyrin (PtOEP)), a carotenoid (e.g. a carotene such as 0-carotene and derivatives), a light-emitting molecule (e.g. 2-(2-hydroxyphenylbenzoxazole) lithium (LiPBO), 4,4'-N, N'4,4'-N,N'-dicarbazole-biphenyl (CBP), (6,6'-bis(1-(2,2'-dicyano)vinyl)-N,N'-dioctyl-3,3'-bicarbazyl (OcCz2CN)$_2$, poly(9,9-dioctylfluorene-alt-benzothiadiazole) (F8BT), poly (9,9-diarylfluorene-alt-benzothiadiazole) (FDFBT), poly(9, 9-diarylfluorene-4-carbazole-alt-benzothiadiazole) (FCzBT), and any combination thereof. In some embodiments, the dopant comprises a plurality of delocalized pi-electrons. In some embodiments, the dopant comprises a conjugated pi-electron system. Such conjugated systems are well known in the art comprising a plurality of adjacent double bonds.

The term "dopant" as used herein refers to a substance used to produce a desired electrical characteristic in a semiconductor. This results in a material with predominantly negative (n-type) or positive (p-type) charge carriers depending on the dopant variety. The term "dopant," as used herein, refers to a doping agent, such as an n-type dopant or a p-type dopant. In some embodiments, the dopant is selected from hemin or poly(9,9-dioctylfluorene-alt-benzothiadiazole) (F8BT).

In some embodiments, the dopant comprises any of F4TCNQ, P3HT, α-NPD or any other organic molecule (e.g. organic dopant) known in the art.

In some embodiments, the composition comprises the dopant at a weight ratio between 0.001% and 5% (w/w), 0.001% and 0.01% (w/w), 0.01% and 0.1% (w/w), 0.1% and 0.5% (w/w), 0.5% and 1% (w/w), 1% and 2% (w/w), 2% and 3% (w/w), or 3% and 5% (w/w), including any range therebetween, wherein the dopant comprises the organic molecule.

In some embodiments, the composition comprises the dopant at a concentration between 0.001 mM and 5 mM, 0.001 mM and 0.01 mM, 0.01 mM and 0.1 mM, 0.1 mM and 0.5 mM, 0.5 mM and 5 mM, 0.5 mM and 1 mM, 1 mM and 2 mM, or 2 mM and 3 mM, including any range therebetween.

In some embodiments, the composition comprises the dopant at a weight ratio between 0.001% and 5% (w/v), 0.001% and 0.01% (w/v), 0.01% and 0.1% (w/v), 0.1% and 0.5% (w/v), 0.5% and 1% (w/v), 1% and 2% (w/v), 2% and 3% (w/v), or 3% and 5% (w/v), including any range therebetween.

In some embodiments, the composition comprises the dopant at a weight ratio between 0.001% and 5% (w/w), 0.001% and 0.01% (w/w), 0.01% and 0.1% (w/w), 0.1% and 0.5% (w/w), 0.5% and 1% (w/w), 1% and 2% (w/w), 2% and 3% (w/w), or 3% and 5% (w/w), including any range therebetween.

One skilled in the art will appreciate, that the exact concentration of the dopant may vary, depending on chemical composition and initial conductivity of the protein, on the chemical composition of the dopant, and/or on the desired conductivity of the composition (e.g. comprising the dropped protein). The concentration of the dopant can be easily adjusted by performing conductivity measurements of the dropped protein films, based on common experimental practice.

In some embodiments, a composition according to the present invention, further comprises a chemical modification. In some embodiments, a chemical modification is selected from sulfonation, phosphorylation, carboxylation, amide bond formation, glycosylation, or any combination thereof.

In some embodiments, a chemical modification comprises the coupling of an organic moiety, inorganic moiety, or both. In some embodiments, the coupling of an organic moiety, inorganic moiety, or both is done via the native amino acid side chain functionality (—NH$_2$, —COOH, OH, or —SH).

In some embodiments, a composition according to the present invention, further comprises a light activated molecule. In some embodiments, a light activated molecule reacts with the free primary amines within the film belonging to lysine residues. In some embodiments, a light activated molecule is covalently bound to the film. In some embodiments, a light activated molecule is a photobase generator. In some embodiments, a light activated molecule is a photoacid generator. The term "photobase generator" as used herein, refers to a photosensitive material that forms a base moiety upon exposure to a light source. The term "photoacid generator" as used herein, refers to a photosensitive material that forms an acid moiety upon exposure to a light source. Any materials that can generate an acid moiety upon irradiation are suitable for the present invention. In some embodiments, the photoacid generator is 8-hydroxypyren-1,3,6-trisulfonic acid (HPTS, pyranine).

In some embodiments, a composition according to the present invention, further comprises a dopant, a chemical modification, a light activated molecule, or any combination thereof. In some embodiments, a composition comprising a dopant, a chemical modification, a light activated molecule, or any combination thereof, is characterized by an increased conductivity. In some embodiments, a composition comprising a dopant, a chemical modification, a light activated molecule, or any combination thereof, is characterized by a conductivity at least 1 mS cm$^{-1}$, at least 2 mS cm$^{-1}$, at least 5 mS cm$^{-1}$, at least 9 mS cm$^{-1}$, at least 10 mS cm$^{-1}$, at least 12 mS cm$^{-1}$, at least 1 mS cm$^{-1}$, at least 15 mS cm$^{-1}$, at least 20 mS cm$^{-1}$, or at least 50 mS cm$^{-1}$ higher than a corresponding composition devoid of a dopant, a chemical modification, a light activated molecule, or any combination thereof.

In some embodiments, a composition according to the present invention is characterized by a conductivity in the range of 0.1 mS cm$^{-1}$ to 100 mS cm$^{-1}$, 0.1 mS cm$^{-1}$ to 90 mS cm$^{-1}$, 0.1 mS cm$^{-1}$ to 85 mS cm$^{-1}$, of 0.1 mS cm$^{-1}$ to 80 mS cm$^{-1}$, 0.1 mS cm$^{-1}$ to 75 mS cm$^{-1}$, 0.1 mS cm$^{-1}$ to 70 mS cm$^{-1}$, 0.1 mS cm$^{-1}$ to 60 mS cm$^{-1}$, 0.1 mS cm$^{-1}$ to 50 mS cm$^{-1}$, 1.5 mS cm$^{-1}$ to 100 mS cm$^{-1}$, 1.5 mS cm$^{-1}$ to 99 mS cm$^{-1}$, 1.5 mS cm$^{-1}$ to 98 mS cm$^{-1}$, 1.5 mS cm$^{-1}$ to 95 mS cm$^{-1}$, 1.5 mS cm$^{-1}$ to 90 mS cm$^{-1}$, 1.5 mS cm$^{-1}$ to 85 mS cm$^{-1}$, 1.5 mS cm$^{-1}$ to 80 mS cm$^{-1}$, 1.5 mS cm$^{-1}$ to 75 mS cm$^{-1}$, 1.5 mS cm$^{-1}$ to 70 mS cm$^{-1}$, 1.5 mS cm$^{-1}$ to 60 mS cm$^{-1}$, or 1.5 mS cm$^{-1}$ to 50 mS cm$^{-1}$, including any range therebetween. In some embodiments, conductivity is ionic conductivity. In some embodiments, the conductivity is protonic conductivity. In some embodiments, conductivity is electronic conductivity.

In some embodiments, a composition according to the present invention, is characterized by a conductance in the range of 0.1 mS cm$^{-1}$ to 100 mS cm$^{-1}$. In some embodiments, a composition according to the present invention, is characterized by a a conductance in the range of 0.1 mS cm$^{-1}$ to 100 mS cm$^{-1}$, 0.1 mS cm$^{-1}$ to 90 mS cm$^{-1}$, 0.1 mS cm$^{-1}$ to 85 mS cm$^{-1}$, of 0.1 mS cm$^{-1}$ to 80 mS cm$^{-1}$, 0.1 mS cm$^{-1}$ to 75 mS cm$^{-1}$, 0.1 mS cm$^{-1}$ to 70 mS cm$^{-1}$, 0.1 mS cm$^{-1}$ to 60 mS cm$^{-1}$, 0.1 mS cm$^{-1}$ to 50 mS cm$^{-1}$, 1.5 mS cm$^{-1}$ to 100 mS cm$^{-1}$, 1.5 mS cm$^{-1}$ to 99 mS cm$^{-1}$, 1.5 mS cm$^{-1}$ to 98 mS cm$^{-1}$, 1.5 mS cm$^{-1}$ to 95 mS cm$^{-1}$, 1.5 mS cm$^{-1}$ to 90 mS cm$^{-1}$, 1.5 mS cm$^{-1}$ to 85 mS cm$^{-1}$, 1.5 mS cm$^{-1}$ to 80 mS cm$^{-1}$, 1.5 mS cm$^{-1}$ to 75 mS cm$^{-1}$, 1.5 mS cm$^{-1}$ to 70 mS cm$^{-1}$, 1.5 mS cm$^{-1}$ to 60 mS cm$^{-1}$, or 1.5 mS cm$^{-1}$ to 50 mS cm$^{-1}$, including any range therebetween. In some embodiments, conductance is ionic conductance. In some embodiments, the conductance is protonic conductance. In some embodiments, conductance is electronic conductance.

In some embodiments, a composition according to the present invention, is used in fuel cell configuration, optogenetics, tissue engineering, organic field effect transistors (OFET), organic light emitting diodes (OLED) and organic photovoltaic cells (OPV), flexible electronics, electrodes, implantable electronic devices (CIEDs), or electrodes for human machine interfaces (HMI). In some embodiments, a composition according to the present invention, is for use in electrodes for fuel cells. In some embodiments, a composition according to the present invention, is used in electrodes for medical applications, such as electrocardiogram (EGC), electroencephalogram (EEG), electrooculogram (EOG), electroconvulsive therapy (ECT), or defibrillator.

Articles

According to an aspect of some embodiments of the present invention there is provided an article which comprises a composition as described elsewhere herein. In some embodiments, the article is, or is incorporated into, a device.

According to an aspect of some embodiments of the present invention there is provided an article which comprises a composition comprising an at least partially denatured protein and one or more crosslinkers, wherein the composition is characterized by a conductivity in the range of 0.1 mS cm$^{-1}$ to 100 mS cm$^{-1}$, 1.5 mS cm$^{-1}$ to 100 mS cm$^{-1}$, 1.5 mS cm$^{-1}$ to 99 mS cm$^{-1}$, of 1.5 mS cm$^{-1}$ to 98 mS cm$^{-1}$, of 1.5 mS cm$^{-1}$ to 95 mS cm$^{-1}$, of 1.5 mS cm$^{-1}$ to 90 mS cm$^{-1}$, of 1.5 mS cm$^{-1}$ to 85 mS cm$^{-1}$, of 1.5 mS cm$^{-1}$ to 80 mS cm$^{-1}$, 1.5 mS cm$^{-1}$ to 75 mS cm$^{-1}$, of 1.5 mS cm$^{-1}$ to 70 mS cm$^{-1}$, of 1.5 mS cm$^{-1}$ to 60 mS cm$^{-1}$, or 1.5 mS cm$^{-1}$ to 50 mS cm$^{-1}$, including any range therebetween.

According to an aspect of some embodiments of the present invention there is provided an article which comprises a composition comprising an at least partially denatured protein and one or more crosslinkers, wherein the composition is characterized by a transparency in the range of 95% to 100%.

According to an aspect of some embodiments of the present invention there is provided an article which comprises a composition comprising an at least partially denatured protein and one or more crosslinkers, wherein the composition is characterized a Young's Modulus of 1 MPa to 50 MPa.

In some embodiments, a composition further comprises a dopant, or a chemical modification.

In some embodiments, a composition further comprises alight activated molecule. In some embodiments, a light activated molecule is a photobase generator. In some embodiments, a light activated molecule is a photoacid generator.

In some embodiments, the composition is characterized by a conductivity in the range of 1.5 mS cm$^{-1}$ to 100 mS cm$^{-1}$, 0.5 mS cm$^{-1}$ to 99 mS cm$^{-1}$, of 1.5 mS cm$^{-1}$ to 98 mS cm$^{-1}$, of 1.5 mS cm$^{-1}$ to 95 mS cm$^{-1}$, 1.5 mS cm$^{-1}$ to 90 mS cm$^{-1}$, of 1.5 mS cm$^{-1}$ to 85 mS cm$^{-1}$, of 1.5 mS cm$^{-1}$ to 80 mS cm$^{-1}$, 1.5 mS cm$^{-1}$ to 75 mS cm$^{-1}$, of 1.5 mS cm$^{-1}$ to 70 mS cm$^{-1}$, of 1.5 mS cm$^{-1}$ to 60 mS cm$^{-1}$, or 1.5 mS cm$^{-1}$ to 50 mS cm$^{-1}$, including any range therebetween.

In some embodiments, the composition is characterized by a conductance in the range of 1.5 mS cm$^{-1}$ to 100 mS cm$^{-1}$. In some embodiments, a composition has a conductance in the range of 1.5 mS cm$^{-1}$ to 99 mS cm$^{-1}$, of 1.5 mS cm$^{-1}$ to 98 mS cm$^{-1}$, of 1.5 mS cm$^{-1}$ to 95 mS cm$^{-1}$, 1.5 mS cm$^{-1}$ to 90 mS cm$^{-1}$, of 1.5 mS cm$^{-1}$ to 85 mS cm$^{-1}$, of 1.5 mS cm$^{-1}$ to 80 mS cm$^{-1}$, 1.5 mS cm$^{-1}$ to 75 mS cm$^{-1}$, of 1.5 mS cm$^{-1}$ to 70 mS cm$^{-1}$, of 1.5 mS cm$^{-1}$ to 60 mS cm$^{-1}$, or 1.5 mS cm$^{-1}$ to 50 mS cm$^{-1}$, including any range therebetween. In some embodiments, conductance is ionic conductance. In some embodiments, conductance is electron conductance.

In some embodiments, a composition has a thickness in the range of 1 µm to 1000 µm. In some embodiments, a composition has a thickness in the range of 5 µm to 1000 µm, 10 µm to 1000 µm, 20 µm to 1000 µm. 20 µm to 1000 µm. 30 µm to 1000 µm, 50 µm to 1000 µm, 100 µm to 1000 µm, 300 µm to 1000 µm, 500 µm to 1000 µm, 20 µm to 500 µm, 20 µm to 100 µm, 1 µm to 100 µm, or 1 µm to 50 µm, including any range therebetween.

In some embodiments, the composition is in the form of a coating on the article.

In some embodiments, the composition is in the form of support for the article, such as an electrode.

In some embodiments, the article is biocompatible. In some embodiments, the article is an electrode. In some embodiments, the article is an electrocardiogram (ECG) electrode. In some embodiments, the article is an electrooculogram (EOG) electrode. In some embodiments, the article is an electroencephalogram (EEG) electrode.

In some embodiments, the electrode comprises a substrate. In some embodiments, the substrate comprises any conducting material or combination of conducting and non-conducting materials. Non-limiting examples of electrically conductive substrates can be manufactured from metals including, but not limited to: Gold (Au), Platinum (Pt), Iridium (Ir), Palladium (Pd), Tungsten (W), Nickel (Ni), Copper (Cu) Aluminum (Al), Stainless Steel (SS), Indium-Tin-Oxide (ITO), Zinc (Zn), Titanium (Ti), Tungsten (W) and their alloys and oxides. Other electrically conductive substrates can include: carbon, carbon fiber, glassy carbon, carbon composites, carbon paste, conductive ceramics, for example, doped silicon (Si), conductive monomers and polymers. In some embodiments, the substrate is in contact or coupled with a composition as described elsewhere herein.

Method

According to an aspect of some embodiments of the present invention there is provided a method for preparing a composition according to the present intention, comprising the steps of contacting a protein with a solvent, thereby obtaining a solution, contacting the solution with one or more denaturing agents and a crosslinker; and allowing the solvent to evaporate, thereby forming the composition of the present invention.

In some embodiments, contacting comprises dissolving. In some embodiments, contacting comprises mixing.

According to an aspect of some embodiments of the present invention there is provided a method for preparing a composition according to the present intention, comprising the steps of dissolving a protein in a solvent obtaining a solution, adding one or more denaturing agents and a crosslinker to the solution and allowing the solvent to evaporate, thereby forming a film.

In some embodiments, the solution is mixed thoroughly under strong vortex. In some embodiments, the solution is mixed for 10 minutes (min) to 3 hours (h). In some embodiments, the solution is mixed for 20 min to 3 h, 10 min to 2 h, 10 min to 1 h, or 30 min to 2 h, including any range therebetween.

In some embodiments, a crosslinker is in a solution. In some embodiments, a crosslinker is in an ethanol solution. In some embodiments, a crosslinker comprises an amine, diamine or a dithiol. In some embodiments, a crosslinker comprises a diamine. In some embodiments, a crosslinker comprises ethylenediamine. In some embodiments, the formation of a film using a diamine is at least 1 fold, at least 2 fold, at least 3 fold, at least 4 fold, at least 5 fold, at least 6 fold, or at least 10 fold faster than the formation of a film using an amine.

In some embodiments, the solvent comprises 2,2,2-Trifluoroethanol (TFE), water or a mixture thereof. In some embodiments, TFE and water are used in a ratio of 100% TFE to 1:1 (TFE:water). In some embodiments, the solvent comprises TFE, water or a mixture thereof. In some embodiments, TFE and water are used in a ratio of 98:2 to 2:1, 95:5 to 2:1, 9:1 to 2:1, 100% TEF to 10:1, 100% TEF to 5:1, or 100% TEF to 4:1, or 100% TEF to 2:1, including any range therebetween.

In some embodiments, the protein and the crosslinker are used in a ratio of 100:0.01 to 100:1. In some embodiments, the protein and the crosslinker are used in a ratio of 100:0.05 to 100:1, 100:0.1 to 100:1, 100:0.15 to 100:1, 100:0.2 to 100:1, 100:0.1 to 100:0.5, 100:0.1 to 100:0.15, 100:0.1 to 100:0.2, or 100:0.1 to 100:0.9, including any range therebetween.

In some embodiments, the protein and the crosslinker are used in a ratio of at least 100:1. In some embodiments, the protein and the crosslinker are used in a ratio of at least 100:1, at least 150:1, at least 200:1, at least 250:1, at least 300:1, at least 500:1, or at least 500:1, including any range therebetween.

In some embodiments, the method of the present invention further comprises a step of contacting the composition with a dopant, a chemical modification, a light activated molecule or a combination thereof. In some embodiments, the composition is in the form of a film.

General

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non-limiting fashion.

Example 1

Albumin Based Films

Bovine serum albumin (BSA) proteins were used as starting material. Conductive polymers out of BSA were made. The same process can be applied for human serum albumin (HSA) also. Both the proteins are commercially available in large quantity by various providers such as Sigma-Aldrich. In the inventors typical procedure 14 wt % BSA is dissolved in 2,2,2-Trifluoroethanol (TFE):$H_2O$ (4:1) mixture in a 20 mL glass vial. The solution is mixed thoroughly under strong vortex for 1 hr to get a clear solution. Then 6% 2-Mercaptoethanol is added, and mixed thoroughly under strong vortex for 20 min, which causes the solution to become cloudy. This is followed by the addition of 100 μL/mL of ethylenediamine ethanol mixture (1:1), which immediately whitens the solution. The final mixture is stirred under strong vortex for few minutes until it becomes clear (not white). This mixture is then drop casted to a desired surface (such as Petri dish), and kept at room temperature overnight covered by a lid to allow slow evaporation of solvent and a transparent film is formed. The film can be taken out from the petri dish with the help of a spatula/tweezers (FIG. 1). The measured conductivity of the film is 0.7 mS cm$^1$, which the inventors ascribe to ionic conductance.

Example 2

Albumin Based Films with Increased Conductivity

Figure 2:
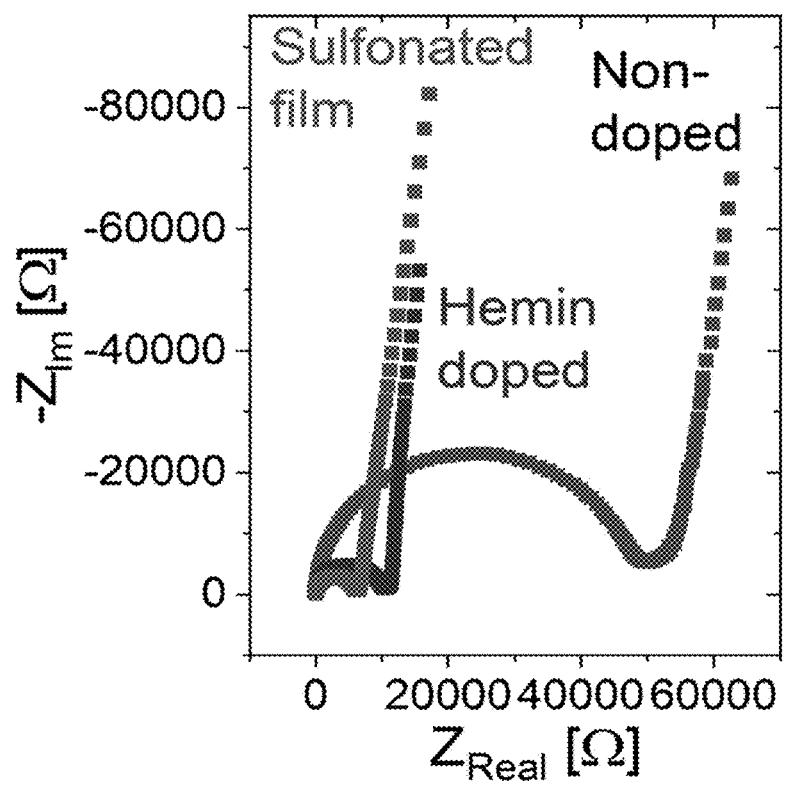
FIG. 2 presents a Nyquist plot of the impedance spectra of the native protein film, hemin doped film and sulphonated film.

To increase the conductivity of the film different modification can be done. One methodology is to sulphonate the film to increase its protonic conductivity. For this purpose, a piece of BSA film (in a desired size, we use 1×5 cm) is placed in a 50 ml round bottom flask fitted with a septum. All air inside is removed by applying vacuum and nitrogen is purged into the flask, followed by the addition of 10 mL of dry DCM and 0.12 M chlorosulfonic acid. The mixture is kept under stirring condition in a nitrogen atmosphere for several hour. Then, the film is washed thoroughly with water. As a result of the sulphonation process, the measured conductance increases to above 10 mS cm$^{-1}$ (FIG. 2).

To improve electronic conductivity, the film can be doped with Hemin (porphyrin containing iron as electron mediator). A piece of the film is placed in a petri dish containing 0.5 mM of Hemin. The whole solution kept under continuous shaking overnight covered with aluminum foil. The solution become clear and the color of the film become dark red. For the case of hemin doping, the conductivity of the film increases to ~3 mS cm$^{-1}$ (FIG. 2).

To control ionic conductivity by light, photoacids are covalently bound to the material. The photoacid of pyranine can be used. The pyranine molecule is functionalized first by adding acetic anhydride to acetylate its free hydroxyl, followed by adding a thionyl chloride to chlorinate its sulfonate groups. The product is added to a piece of the film in a dry DCM environment with triethylamine (TEA), where the end film product is composed of the pyranine photoacid covalently attached to free primary amines within the film (belongs to lysine residues), and the reactive hydroxyl is deprotected.

Example 3

Protein Based Films Formation

14 Wt % of Bovine serum albumin (BSA) protein was dissolved in TFE:water (4:1) and mixed well on a vortex for 14 hour to get a clear solution. Then, 6% 2-mercaptoethanol was added into the mixture and again vortex for 2.5-3 hour, until the solution becomes cloudy. After that, 5% ethylenediamine was diluted with (1:1) absolute ethanol and added into the mixture. Upon addition some white fibrils appears immediately. Then the reaction mixture was vortexed for 30-40 min to get a clear solution. Finally the clear solution was drop casted to a desired mold (such as a 90 mm borosil petri dish) and kept under well-ventilated area for 6-10 (depending on solvent evaporation rate) hour to obtain a transparent film. After formation, the film was washed several times with distilled water and kept under distilled water at room temperature before further measurement.

When casein protein was used under the same procedure, no film was formed.

Figure 3:
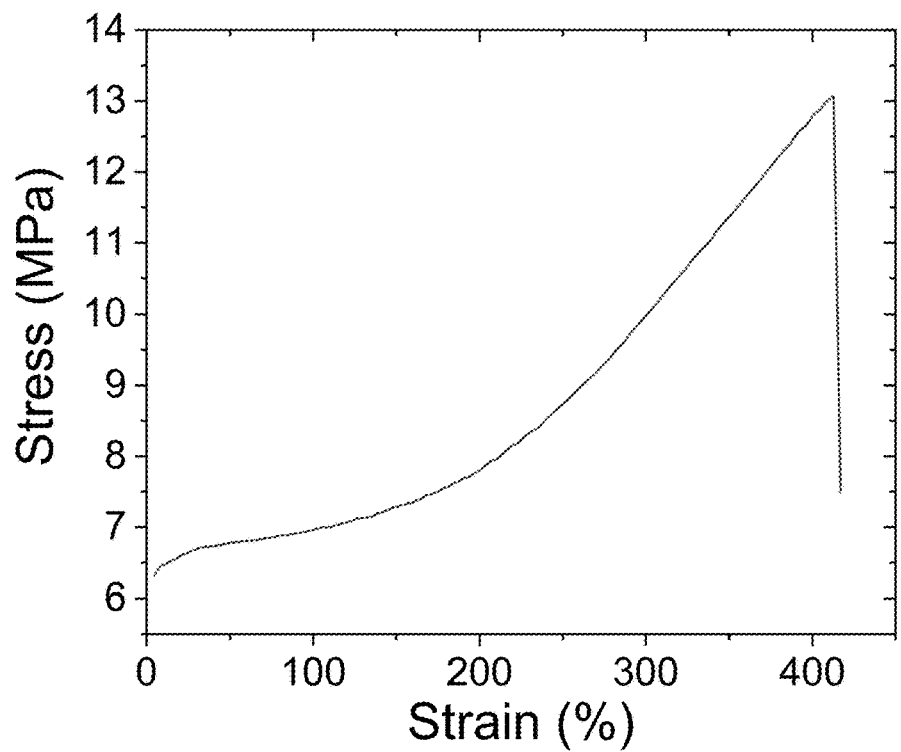
FIG. 3 is a graph presenting the mechanical properties of the BSA film (stress-strain curve)
Figure 4:
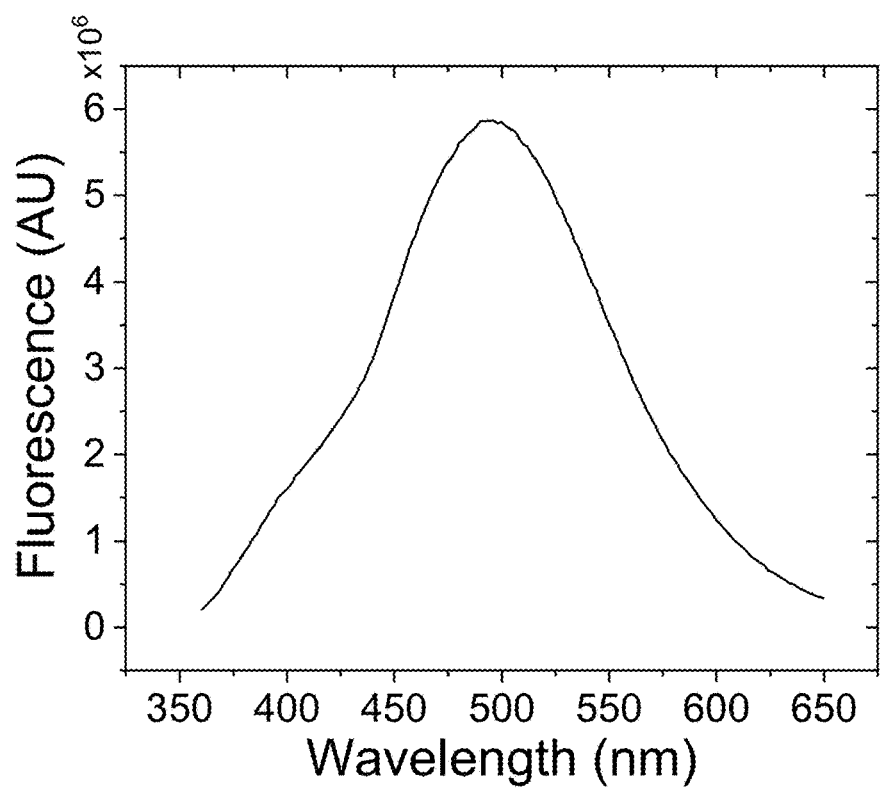
FIG. 4 is a graph presenting the fluorescence properties of the BSA film.

The mechanical properties and fluorescence properties of the BSA film are presented in FIG. 3 and FIG. 4 respectively.

Example 4

Protein Crosslinking

The native Cys residue present inside the protein is used for the crosslinking process, by adding ethylenediamine (EDA) to increase the pH to 9. Different amines have been used such as methyl amine (1° amine), di-methyl amine (2° amine), and tri-methyl amine (3° amine). In all the cases formation of film was observed. However, by using methyl amine, di-methyl amine, or tri-methyl amine, the formation of the film was longer, taking 4-7 days to form. When EDA was used, formation of the film was observed overnight. Without being bound by any particular theory, the efficiency of EDA can be due to presence of two amine functionality.

Example 5

Bovine Serum Albumin (BSA) Film

Bovine serum albumin (BSA) film was obtained by the experimental procedure described in Example 3.

Figure 5:
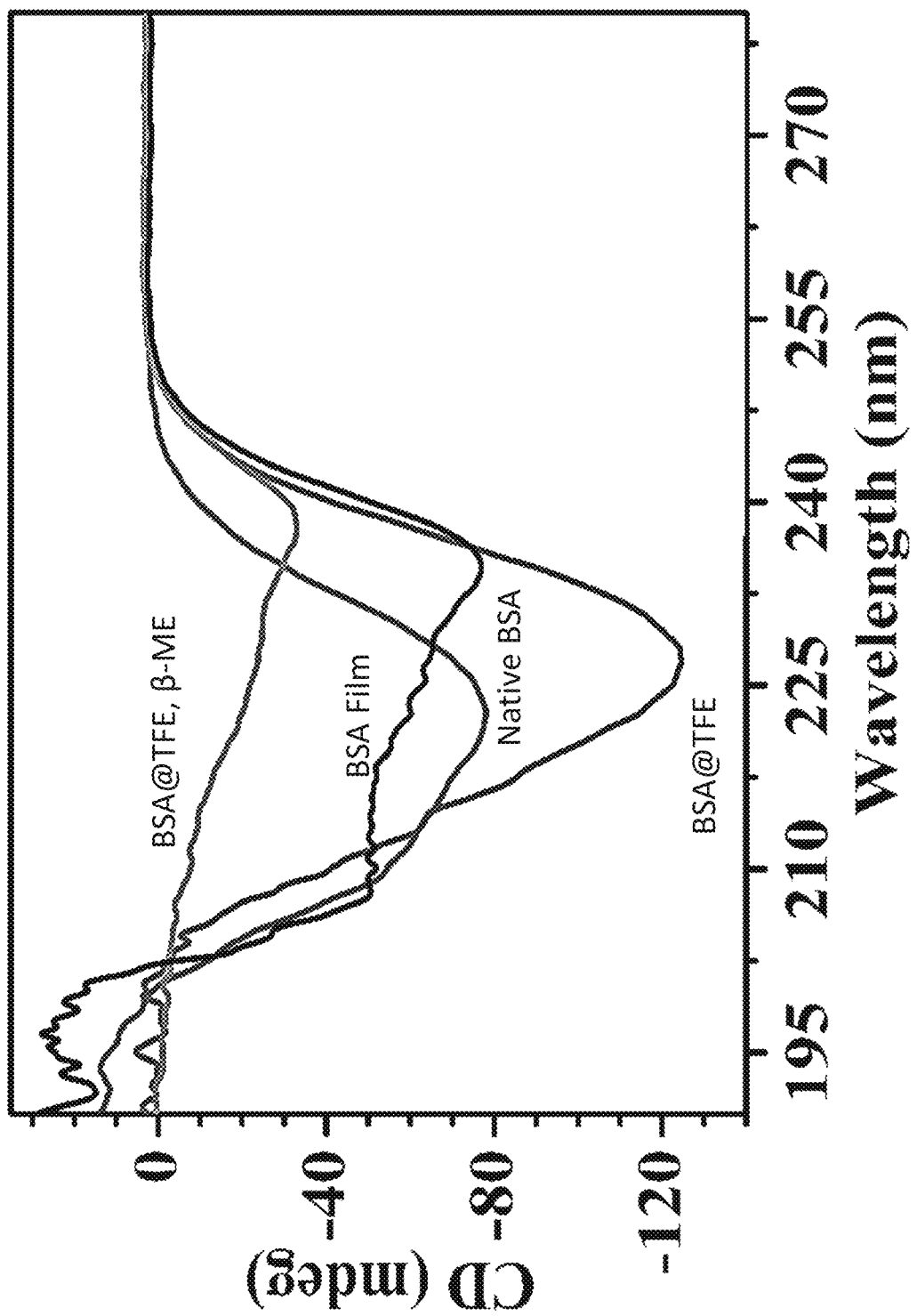
FIG. 5 is a graph presenting the circular dichroism (CD) spectra of BSA protein at different stages of chemical processing: native BSA protein (Native BSA), BSA dissolved in TFE (BSA@TFA); BSA after reduction using 2-mercaptoethanol (BSA@TFE, β-ME), and at the end of polymerization process (BSA film)

Circular dichroism (CD) was used to follow the change in the protein secondary structure during the different stages of the polymerization process (FIG. 5).

Native BSA is a primarily α-helix containing protein, reflected in the common two bands in the CD spectrum, at 208 nm ($\pi \rightarrow \pi^*$) and 222 nm ($n \rightarrow \pi^*$). Upon dissolving the BSA in the acidic TFE solution, the CD spectrum is dominated by a single negative band at 227 nm, indicating the fundamental change in the BSA secondary structure. The reduction of disulfide bonds by 2-mercaptoethanol, results in a further red shifting of the negative CD band to 238 nm with a significant decrease in its intensity, hence reflecting further denaturation of the protein. In the last polymerization step, the addition of ethylenediamine (EDA) to initiate the cross-linking via oxidative disulfide bond formation, the CD spectrum changes, showing both features of the native α-helical protein (the negative band at 208 nm and the positive one at 195 nm) as well as the negative peak of the denatured protein (at 235 nm). The complex CD spectra of the film indicates presence of both alpha helix and beta sheet in the protein structure.

Figure 6:
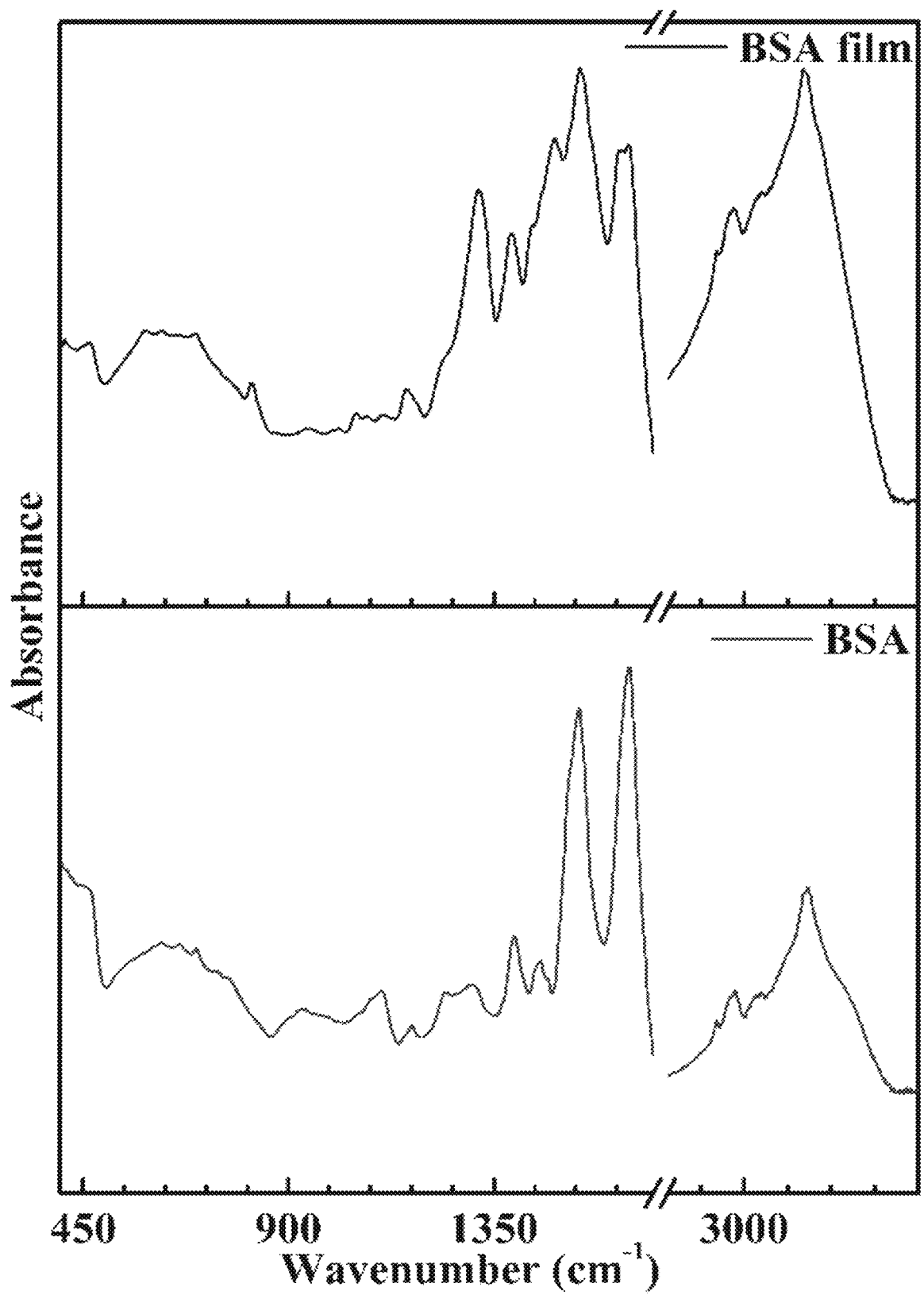
FIG. 6 presents a FTIR spectra of BSA film (top) and native BSA (bottom)

FIG. 6 presents FTIR spectra of BSA film (top) and native BSA (bottom). The sharp peaks of the native BSA (at 1647 and 1537 $cm^{-1}$), corresponding to the α-helical nature of the protein, are clearly changing and exhibiting a double-band for both amide I (1645 and 1625 $cm^{-1}$) and amide II (1539 and 1484 $cm^{-1}$). This complex FTIR signature of the BSA film indicates on the presence of two different types of secondary structures within the BSA film. In addition, the change in the location and intensity of the broad peak at 3600-3000 $cm^{-1}$, corresponding to both —OH and —NH stretching, further indicates a structural change.

Figure 7:
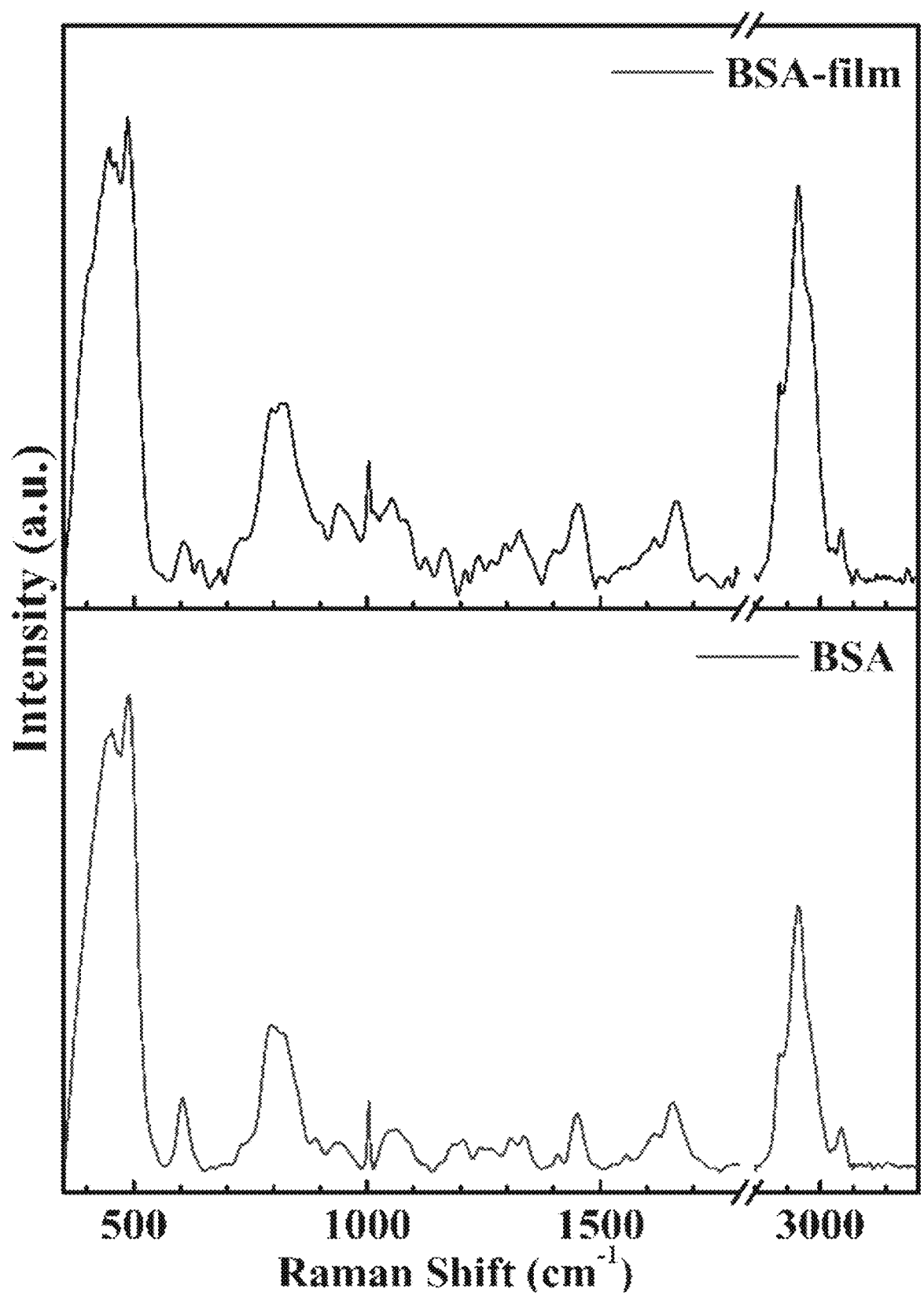
FIG. 7 presents a Raman spectra of BSA film (top) and native BSA (bottom)

FIG. 7 presents Raman spectra of BSA film (top) and native BSA (bottom). The Raman spectrum of native BSA shows sharp peaks at 452 and 489 $cm^{-1}$, which are ascribed to signal from disulfide bonds. These peaks undergo shifting (to 447 and 486 $cm^{-1}$, respectively) following polymerization, indicating a different environment of the disulfide bonds between the native protein (intramolecular bonds) to the formed polymer (intermolecular bonds). Another indication for the structural transition of the protein is the change in the weak double peak of skeletal 6-CH (1280-1350 $cm^{-1}$) that changes from symmetric before polymerization to asymmetric after, and the shift in the amide I band from 1653 $cm^{-1}$ to 1663 $cm^{-1}$. Other peaks, such as the ones of aromatic amino acids (at 1003 $cm^{-1}$) and of water (2860-3000 $cm^{-1}$) do not undergo major changes.

Figure 8:
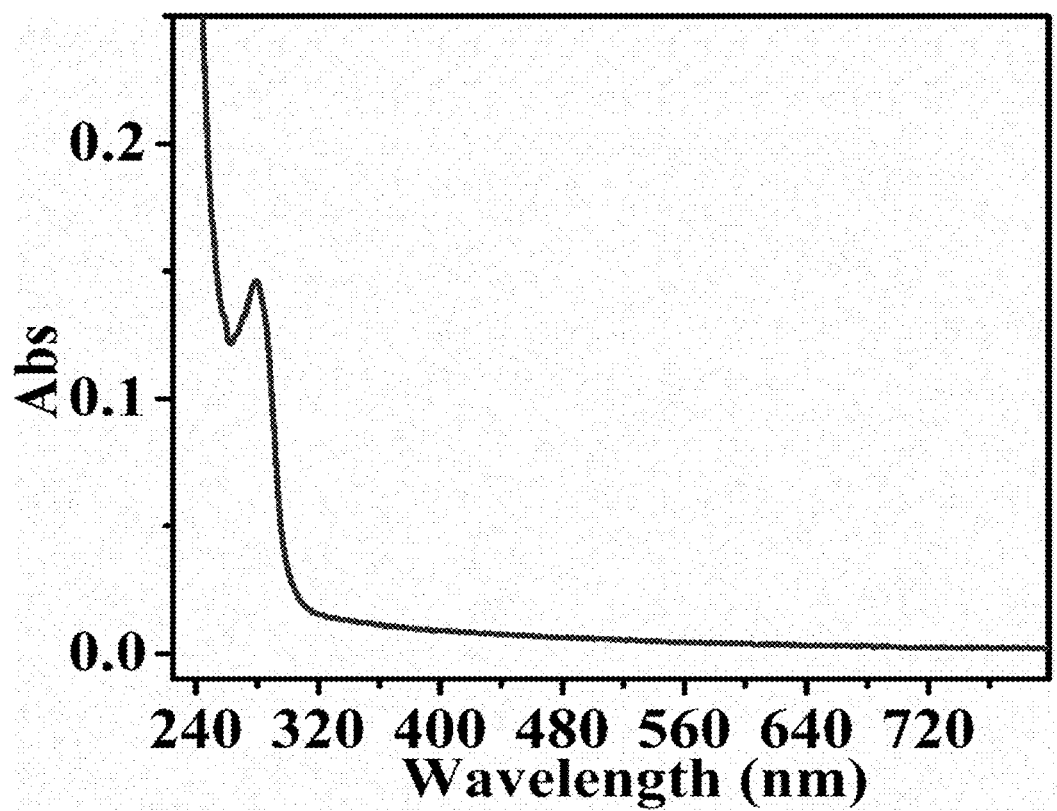
FIG. 8 presents an optical absorption spectra of BSA film in the UV-Vis region.

FIG. 8 represents optical absorption spectra of BSA film in the UV-Vis region, showing the transparency nature of the film across the visible.

Figure 9:
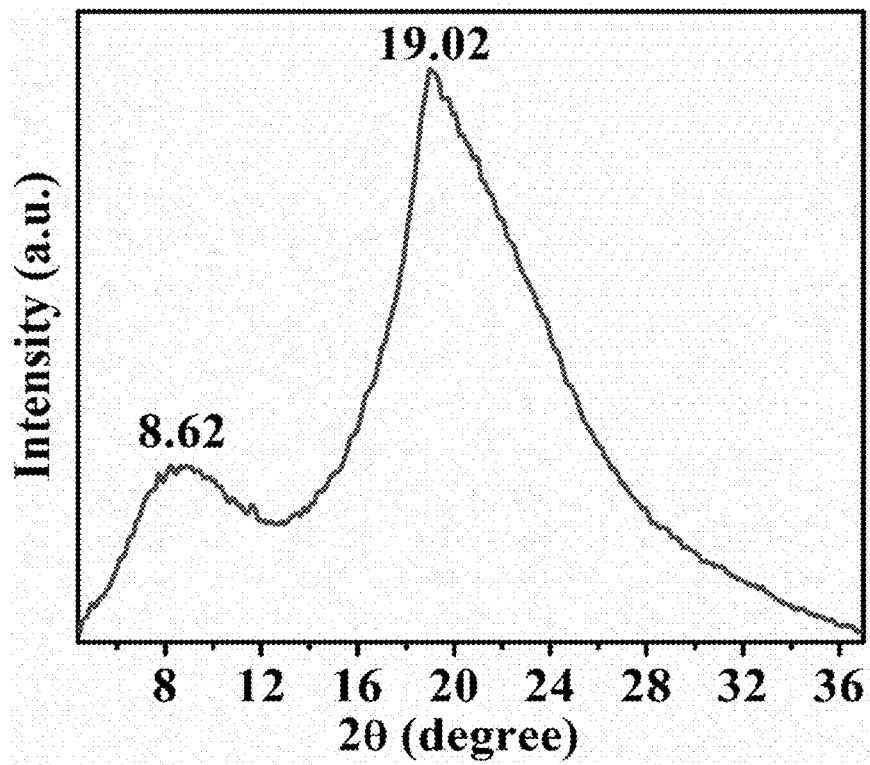
FIG. 9 is a graph presenting a wide-angle x-ray scattering profile of the BSA film.

FIG. 9 shows a wide-angle x-ray scattering profile of the BSA film. Wide-angle x-ray scattering (WAXS) pattern is same in meridional and equatorial direction which suggest a repeating semi crystalline nature of the BSA film in all directions.

Figure 10:
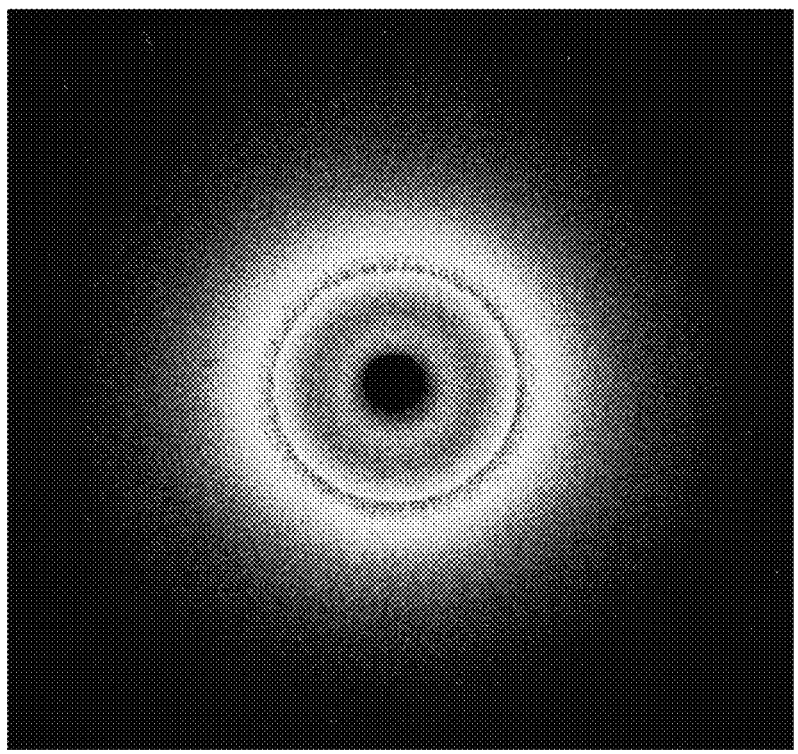
FIG. 10 presents a wide-angle x-ray scattering pattern of the BSA film.

FIG. 10 shows a wide-angle x-ray scattering pattern of the BSA film.

The WAXS measurements shows a repeating pattern typical to a semi-crystalline ordered structure with two peaks at 2θ=8.62 and 19.02, corresponding to distances of 12.3 Å and 5.73 Å, respectively, whereas the larger value (12.3 Å) is associated with the periodic distance between protein chains inside the polymer.

Figure 11:
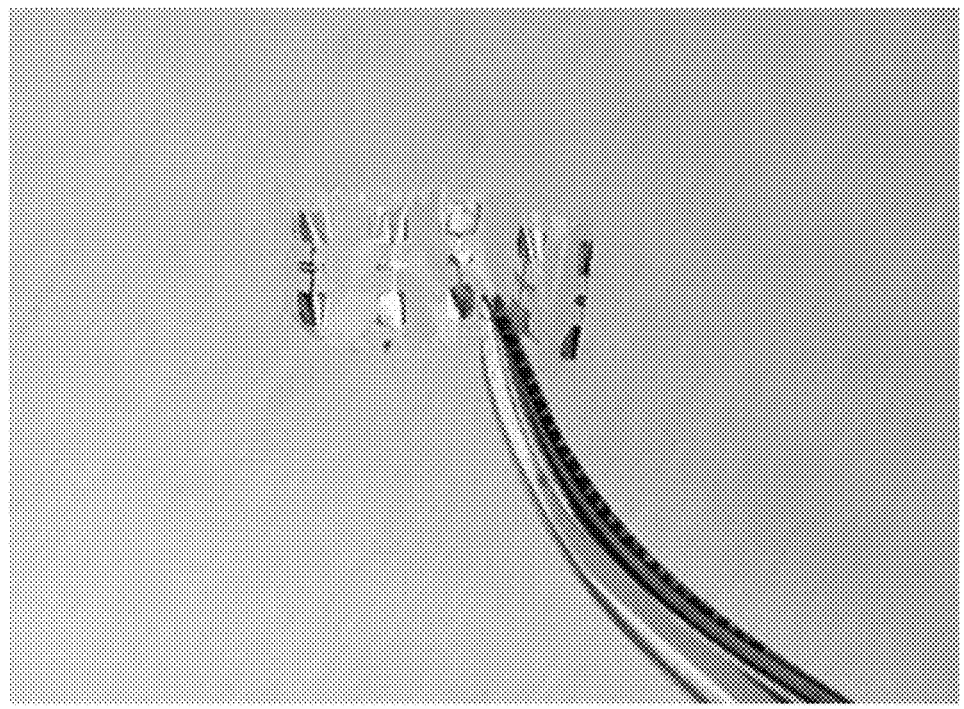
FIG. 11 is a picture presenting a flexible device equipped with gold electrode.

FIG. 11 represents a flexible device equipped with gold electrode. Since the BSA film material is stretchable, transparent, soft, nontoxic to human skin because of its biological nature it ca be used in the field of artificial skin and skin based electronic devices.

Example 6

Bovine Serum Albumin (BSA)-Doped Film

An additional doping example, using poly(9,9-dioctylfluorene-alt-benzothiadiazole) (F8BT) molecule is presented. The doping using F8BT was done following the procedure: 5 mg F8BT was dissolved in 1 ml chloroform and added into the polymer solution mixed well before casting.

Figure 12:
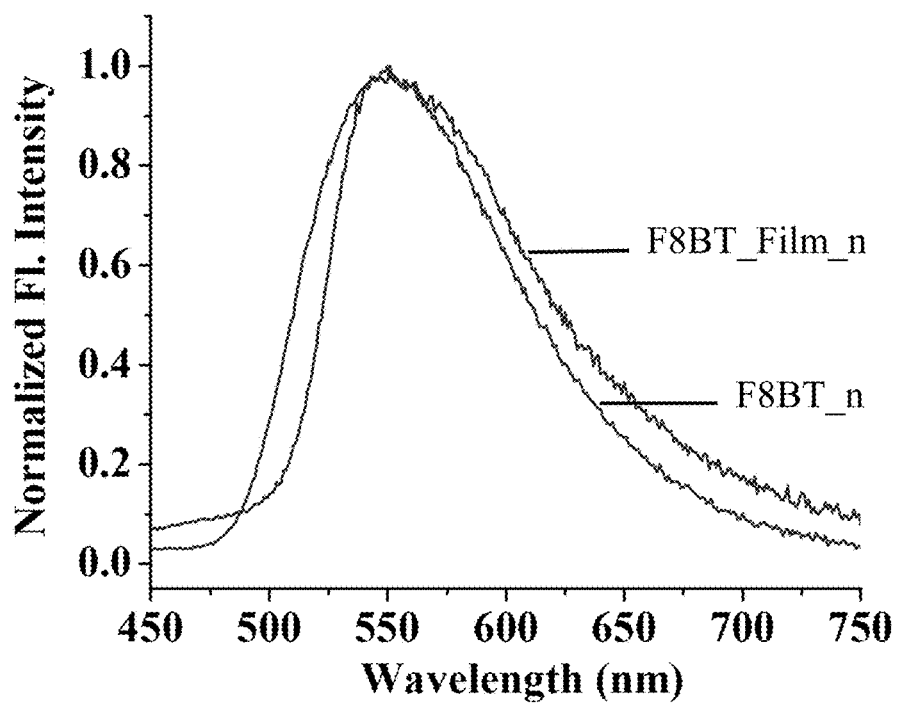
FIG. 12 is a graph of the steady state emission of poly(9,9-dioctylfluorene-alt-benzothiadiazole) (F8BT) polymer in solution (F8BT_n) and inside BSA film (F8BT_Film_n)
Figure 13:
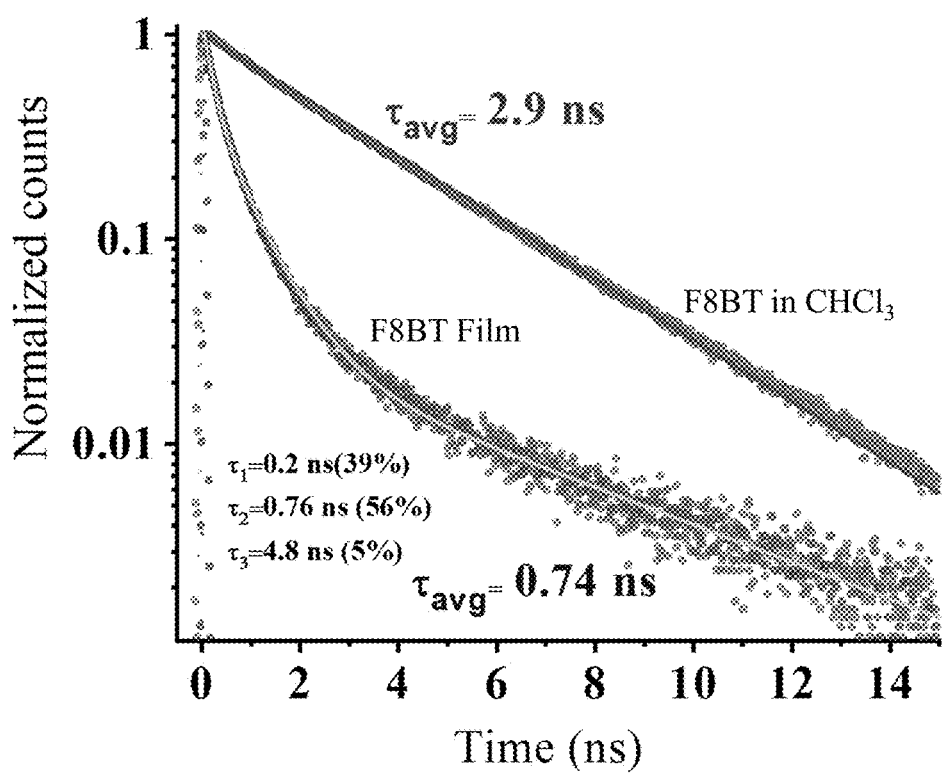
FIG. 13 presents the time resolved emission spectra of F8BT in Chloroform and inside BSA film and corresponding lifetime ($\sigma_{avg}$)
Figure 14:
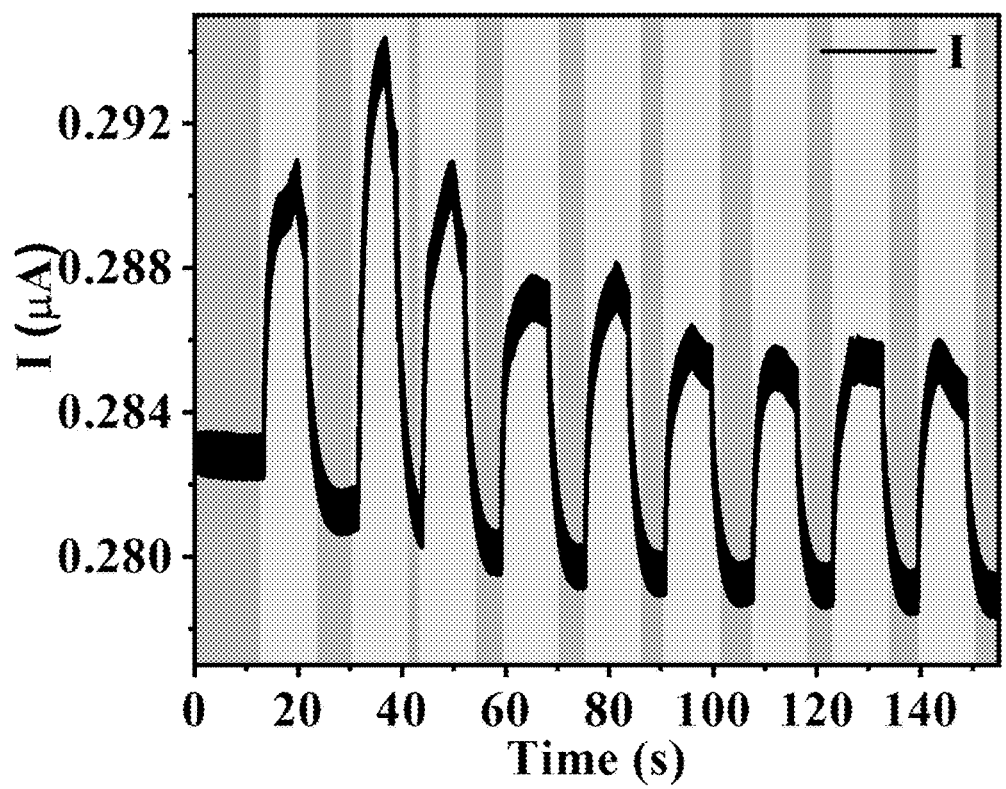
FIG. 14 presents the current response of F8BT doped BSA film as a function of light on/off under zero bias.

Results of the organic polymer doping are presented in FIGS. 12, 13, and 14.

FIG. 12 presents a graph of the steady state emission of poly(9,9-dioctylfluorene-alt-benzothiadiazole) (F8BT) polymer in solution (F8BT_n) and inside BSA film (F8BT_Film_n).

FIG. 13 presents the time resolved emission spectra of F8BT in chloroform and inside BSA film and corresponding lifetime ($\sigma_{avg}$).

FIG. 14 presents the current response of F8BT doped BSA film as a function of light on/off under zero bias.

Figure 15:
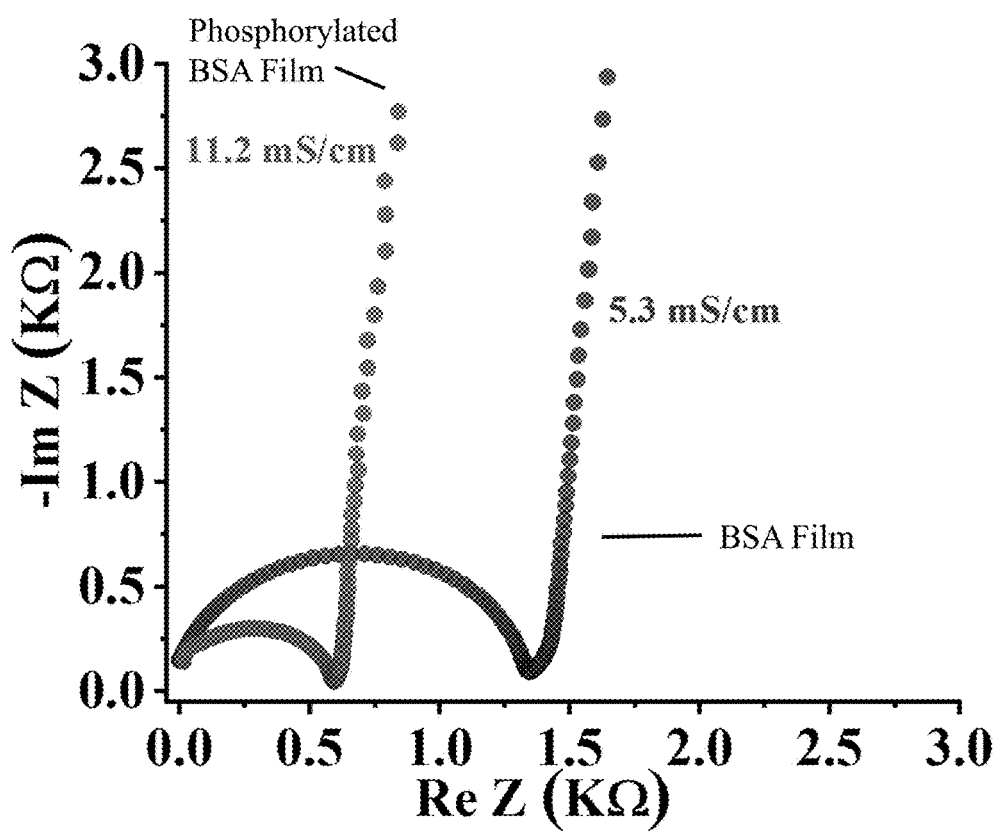
FIG. 15 is a graph of the measured conductivity at 25° C. and 80% relative humidity (RH)

FIG. 15 presents a graph of the measured conductivity at 25° C. and 80% relative humidity (RH) for a BSA film, and corresponding phosphorylated BSA film. It can be seen an increase in the film conductivity from 5.3 mS $cm^{-1}$ to 11.2 mS $cm^{-1}$.

Example 7

BSA Films as Solid-State Electrodes

Experiments were performed with the use of BSA films as solid-state electrodes for physio-electro signal sensing. The results are presented in FIGS. 16A-D.

Figure 16A:
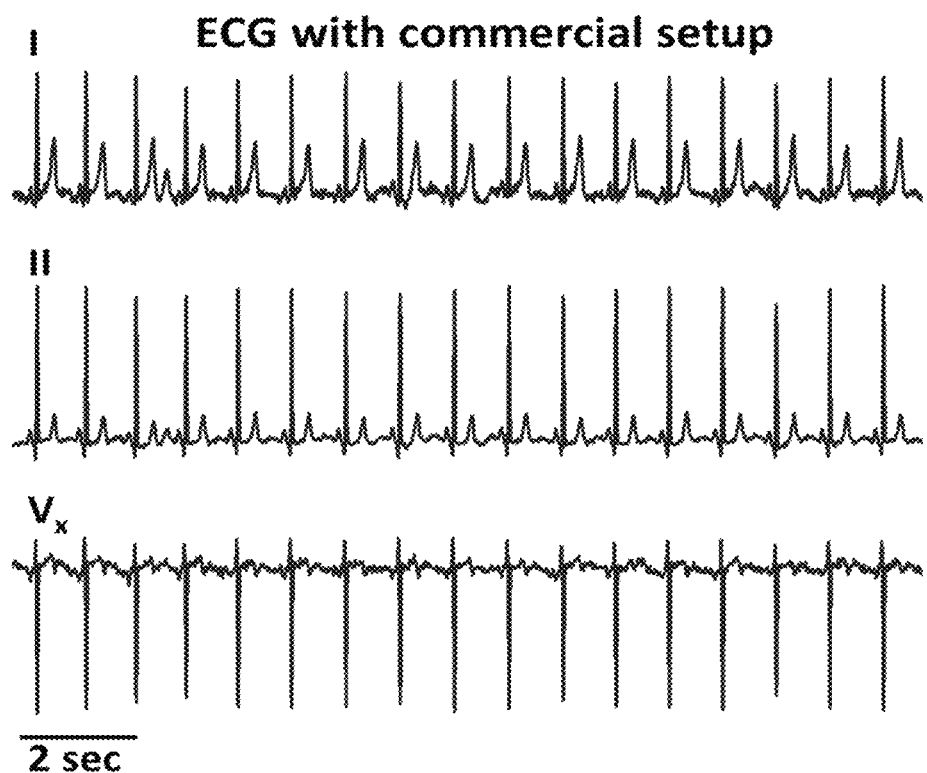
FIGS. 16A-D present an electrocardiogram (EGC) signal recording for the use of BSA film in a standard ECG measurement using 5-electrodes configuration with a commercial recording system. The panel shows the physical recorded three channels (FIG. 16A); an unamplified and unfiltered ECG measurement using 2-electrodes configuration and a source-measuring unit with no application of bias. The inset shows a zoom in on a single peak (FIG. 16B); electroencephalogram (EEG) measurements of a and R waves recordings. The insets show the FFT frequency domain analysis of the recordings (FIG. 16C); and electrooculogram (EOG) measurements of eye blinking recording using 3-electrode configuration (FIG. 16D).
Figure 16B:
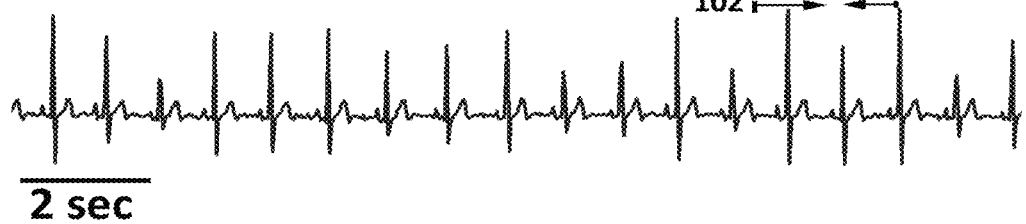
Figure 16C:
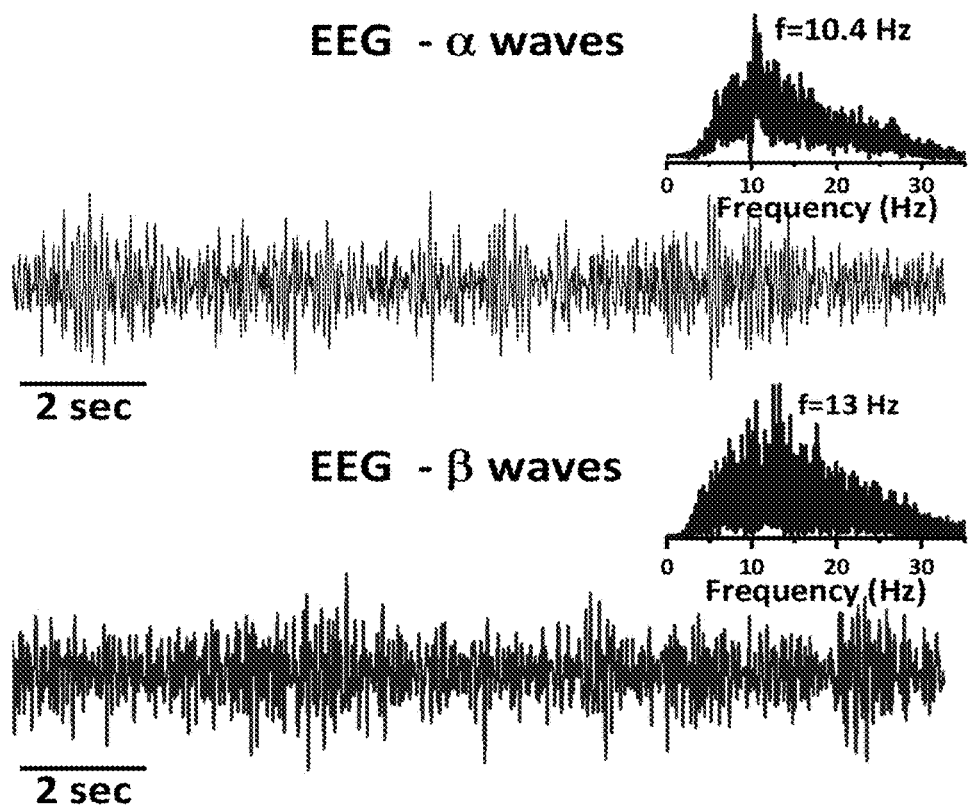
Figure 16D:
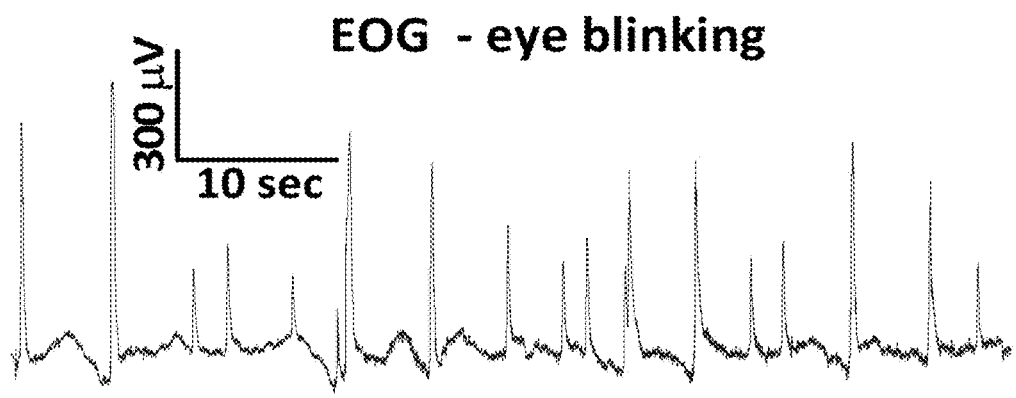

FIG. 16A shows a standard electrocardiogram (ECG) measurement using 5-electrodes configuration with a commercial recording system. FIG. 16B shows an unamplified and unfiltered ECG measurement using 2-electrodes configuration and a source-measuring unit with no application of bias. FIG. 16C shows an electroencephalogram (EEG) measurement of a and p waves recordings. FIG. 16D shows electrooculogram (EOG) measurements of eye blinking recording using 3-electrode configuration.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

The invention claimed is:

1. A composition comprising an at least partially denatured protein crosslinked via one or more covalent cross-linkers, wherein said composition is in a form of a film and is characterized by a conductivity in the range of 0.1 mS $cm^{-1}$ to 1.5 mS $cm^{-1}$; and wherein said composition further comprises a disulfide bond reducing agent comprising one or more thiol containing reducing agents.

2. The composition of claim 1, characterized by a transparency in the range of 95% to 100%; and wherein said disulfide bond reducing agent comprises one or more thiol containing reducing agent, including but not limited to 2-mercaptoethanol, dithiothreitol (DTT), (tris(2-carboxyethyl) phosphine) (TCEP), cysteine, glutathione, a phosphine-containing agent or any combination thereof.

3. The composition of claim 1, characterized by a Young's Modulus in the range of 1 MPa to 50 MPa.

4. The composition of claim 1, characterized by an elastic limit in the range of 100% to 600%.

5. The composition of claim 1, wherein said one or more covalent crosslinkers comprise an amine, diamine or dithiol.

6. The composition of claim 1, wherein said at least partially denatured protein is selected from: (i) a protein crosslinked via amine bonds or disulfide bonds; (ii) a protein characterized by a conductance threshold of at least 0.1 mS cm$^{-1}$; and (iii) a protein comprising albumin.

7. The composition of claim 1, wherein said at least partially denatured protein and said one or more covalent crosslinkers are present within said composition in a weight per weight (w/w) ratio of 100:0.01 to 100:1.

8. The composition of claim 1, comprising 0.01% to 25% (w/w) of said disulfide bond reducing agent.

9. The composition of claim 1, wherein the at least partially denatured protein is bovine serum albumin (BSA) and wherein said one or more covalent crosslinkers is dithiolethylenediamine.

10. The composition of claim 1, characterized by a fluorescence emission in the range of 350 nm to 750 nm.

11. The composition of claim 1, further comprising a dopant, a light activated molecule, or both; optionally wherein said light activated molecule is selected from a photobase generator or a photoacid generator; optionally wherein said dopant is selected from a polymer, an organic molecule, an inorganic molecule, an inorganic nanocrystal, a nanowire, and any combination thereof.

12. The composition of claim 1, further comprising a chemical modification of said at least partially denatured protein selected from fluorination, sulfonation, phosphorylation, carboxylation, amide bond formation, glycosylation, or any combination thereof.

13. The composition of claim 1, characterized by a conductivity in the range of 1.5 mS cm$^{-1}$ to 100 mS cm$^{-1}$.

* * * * *